(12) United States Patent
Madau et al.

(10) Patent No.: US 9,383,579 B2
(45) Date of Patent: Jul. 5, 2016

(54) METHOD OF CONTROLLING A DISPLAY COMPONENT OF AN ADAPTIVE DISPLAY SYSTEM

(75) Inventors: Dinu Petre Madau, Canton, MI (US); Matthew Mark Mikolajczak, Novi, MI (US); Paul Morris, Ann Arbor, MI (US)

(73) Assignee: VISTEON GLOBAL TECHNOLOGIES, INC., Van Buren Township, MI (US)

( * ) Notice: Subject to any disclaimer, the term of this patent is extended or adjusted under 35 U.S.C. 154(b) by 490 days.

(21) Appl. No.: 13/271,843

(22) Filed: Oct. 12, 2011

(65) Prior Publication Data

US 2013/0097557 A1     Apr. 18, 2013

(51) Int. Cl.
*G06F 3/048* (2013.01)
*G02B 27/01* (2006.01)
*A61B 5/18* (2006.01)
*A61B 3/113* (2006.01)
*B60K 35/00* (2006.01)
*G06K 9/00* (2006.01)

(52) U.S. Cl.
CPC ............ *G02B 27/01* (2013.01); *A61B 3/113* (2013.01); *A61B 5/18* (2013.01); *B60K 35/00* (2013.01); *G06K 9/00604* (2013.01); *G06K 9/00845* (2013.01); *B60K 2350/2052* (2013.01); *B60K 2350/352* (2013.01); *B60K 2350/925* (2013.01); *G02B 2027/014* (2013.01); *G02B 2027/0187* (2013.01)

(58) Field of Classification Search
CPC ................................ G06F 7/60; B60W 50/12

USPC .......................................... 715/810; 345/156
See application file for complete search history.

(56) References Cited

U.S. PATENT DOCUMENTS

| | | |
|---|---|---|
| 2,288,430 A | 6/1942 | Bauman |
| 2,445,787 A | 7/1948 | Lilienfeld |
| 3,462,604 A | 8/1969 | Mason |
| 3,514,193 A | 5/1970 | Himmelmann |
| 3,534,273 A | 10/1970 | Thomas |
| 3,583,794 A | 6/1971 | Newman |
| 3,806,725 A | 4/1974 | Leitz |
| 3,864,030 A | 2/1975 | Cornsweet |
| 3,992,087 A | 11/1976 | Flom et al. |
| 4,003,642 A | 1/1977 | Vogeley |
| 4,034,401 A | 7/1977 | Mann |
| 4,075,657 A | 2/1978 | Weinblatt |
| 4,102,564 A | 7/1978 | Michael |
| 4,145,122 A | 3/1979 | Rinard et al. |
| 4,169,663 A | 10/1979 | Murr |
| 4,303,394 A | 12/1981 | Berke et al. |
| 5,604,818 A | 2/1997 | Saitou et al. |
| 6,027,216 A | 2/2000 | Guyton et al. |
| 6,856,873 B2 | 2/2005 | Breed et al. |

(Continued)

*Primary Examiner* — William Bashore
*Assistant Examiner* — Jeanette J Parker
(74) *Attorney, Agent, or Firm* — Fraser Clemens Martin & Miller LLC; J. Douglas Miller

(57) ABSTRACT

An adaptive display system includes a display component to present an image to a user, a sensor for detecting a vision characteristic of the user and generating a sensor signal representing the vision characteristic of the user; and a processor in communication with the sensor and the display component, wherein the processor receives the sensor signal, analyzes the sensor signal based upon an instruction set to determine the vision characteristic of the user, and controls a visual output of the display component based upon the vision characteristic of the user.

9 Claims, 13 Drawing Sheets

(56) References Cited

U.S. PATENT DOCUMENTS

| | | |
|---|---|---|
| 7,333,073 B2 | 2/2008 | Repetto et al. |
| 7,788,008 B2 | 8/2010 | Breed |
| 7,920,102 B2 | 4/2011 | Breed |
| 7,924,146 B2 | 4/2011 | Seder et al. |
| 7,969,383 B2 | 6/2011 | Eberl et al. |
| 2003/0201895 A1* | 10/2003 | Harter et al. .................. 340/575 |
| 2007/0164990 A1* | 7/2007 | Bjorklund ............... G06F 3/017 345/156 |
| 2007/0280505 A1* | 12/2007 | Breed .......................... 382/104 |
| 2010/0121501 A1* | 5/2010 | Neugebauer et al. ............. 701/1 |
| 2010/0238280 A1* | 9/2010 | Ishii ....................... B60K 35/00 348/77 |
| 2011/0254698 A1* | 10/2011 | Eberl .................. G02B 27/017 340/901 |
| 2011/0296343 A1* | 12/2011 | Leung et al. .................. 715/799 |
| 2011/0309924 A1* | 12/2011 | Dybalski et al. .............. 340/438 |
| 2012/0215403 A1* | 8/2012 | Tengler et al. .................. 701/36 |
| 2012/0300061 A1* | 11/2012 | Osman et al. ................. 348/135 |
| 2013/0083025 A1* | 4/2013 | Gibson et al. ................. 345/428 |

* cited by examiner

METHOD OF CONTROLLING A DISPLAY COMPONENT OF AN ADAPTIVE DISPLAY SYSTEM

FIELD OF THE INVENTION

The present invention relates generally to a display system. In particular, the invention is directed to an adaptive display system including at least one display component and a method for controlling a visual output of the at least one display component based on an eye tracking of a user.

BACKGROUND OF THE INVENTION

Eye-tracking devices detect the position and movement of an eye. Several varieties of eye-tracking devices are disclosed in U.S. Pat. Nos. 2,288,430; 2,445,787; 3,462,604; 3,514,193; 3,534,273; 3,583,794; 3,806,725; 3,864,030; 3,992,087; 4,003,642; 4,034,401; 4,075,657; 4,102,564; 4,145,122; 4,169,663; and 4,303,394. Currently, eye tracking devices and methods are implemented in vehicles to detect drowsiness and erratic behavior in a driver of a vehicle, as well as enable hands-free control of certain vehicle systems.

However, drivers are frequently required to make use of display components (e.g. heads-up display, dashboard display, and center stack display) to obtain visual information about the vehicle environment to conduct a range of critical tasks (navigation, monitoring speed and fuel level, entertainment system control, etc.). The limited viewable area of the display components generally requires adjustability, typically achieved through manual control of some kind.

It would be desirable to develop an adaptive display system wherein a display component is automatically configured based upon a vision characteristic of a user to maximize a viewable area of a display component without the requirement of manual manipulation.

SUMMARY OF THE INVENTION

In concordance and agreement with the present invention, an adaptive display system wherein a display component is automatically configured based upon a vision characteristic of a user to maximize a viewable area of a display component without the requirement of manual manipulation, has surprisingly been discovered.

In one embodiment, a method of controlling a display component of a display system of a vehicle comprises the steps of: providing the display component configured to present a menu system to a user; providing a sensor to detect a vision characteristic of a user; determining a field of focus of a user based upon the vision characteristic; determining when the field of focus of the user is in a predetermined region of a menu of the menu system; and controlling a configuration of the menu based upon a current position thereof.

In another embodiment, a method of controlling a display component of a display system of a vehicle comprises the steps of: providing the display component configured to present a menu system to a user, the menu system including a first menu, a second menu, and a third menu; providing a sensor to detect a vision characteristic of a user; determining a field of focus of a user based upon the vision characteristic; determining whether the field of focus of the user is in a predetermined region of one of the menus of the menu system; determining whether a selected one of the menus of the menu system is in a desired position; and controlling a configuration of the selected one of the menus based upon a current position thereof.

In yet another embodiment, a method of controlling a display component of a display system of a vehicle comprises the steps of: providing the display component configured to present a menu system to a user, the menu system including a first menu, a second menu, and a third menu; providing a sensor to detect a vision characteristic of a user; determining a field of focus of a user based upon the vision characteristic; determining whether the field of focus of the user is in a predetermined region of one of the menus of the menu system; and positioning a selected one of the menus of the menu system in a maximized position.

BRIEF DESCRIPTION OF THE DRAWINGS

The above, as well as other advantages of the present invention, will become readily apparent to those skilled in the art from the following detailed description of the preferred embodiment when considered in the light of the accompanying drawings in which.

Figure 1:
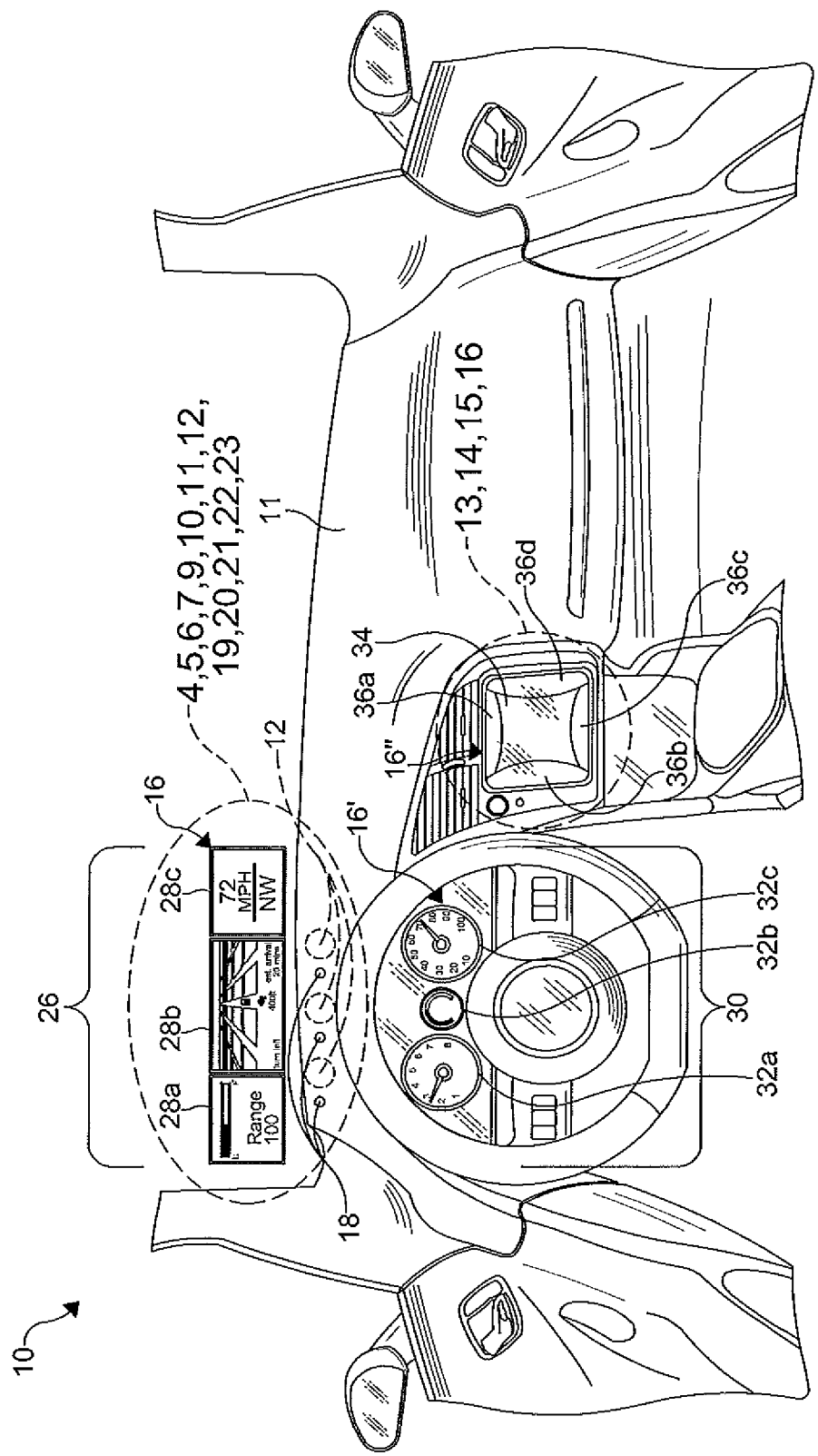
FIG. 1 is a fragmentary schematic perspective view of a vehicle including an adaptive display system according to an embodiment of the present invention.
Figure 2:
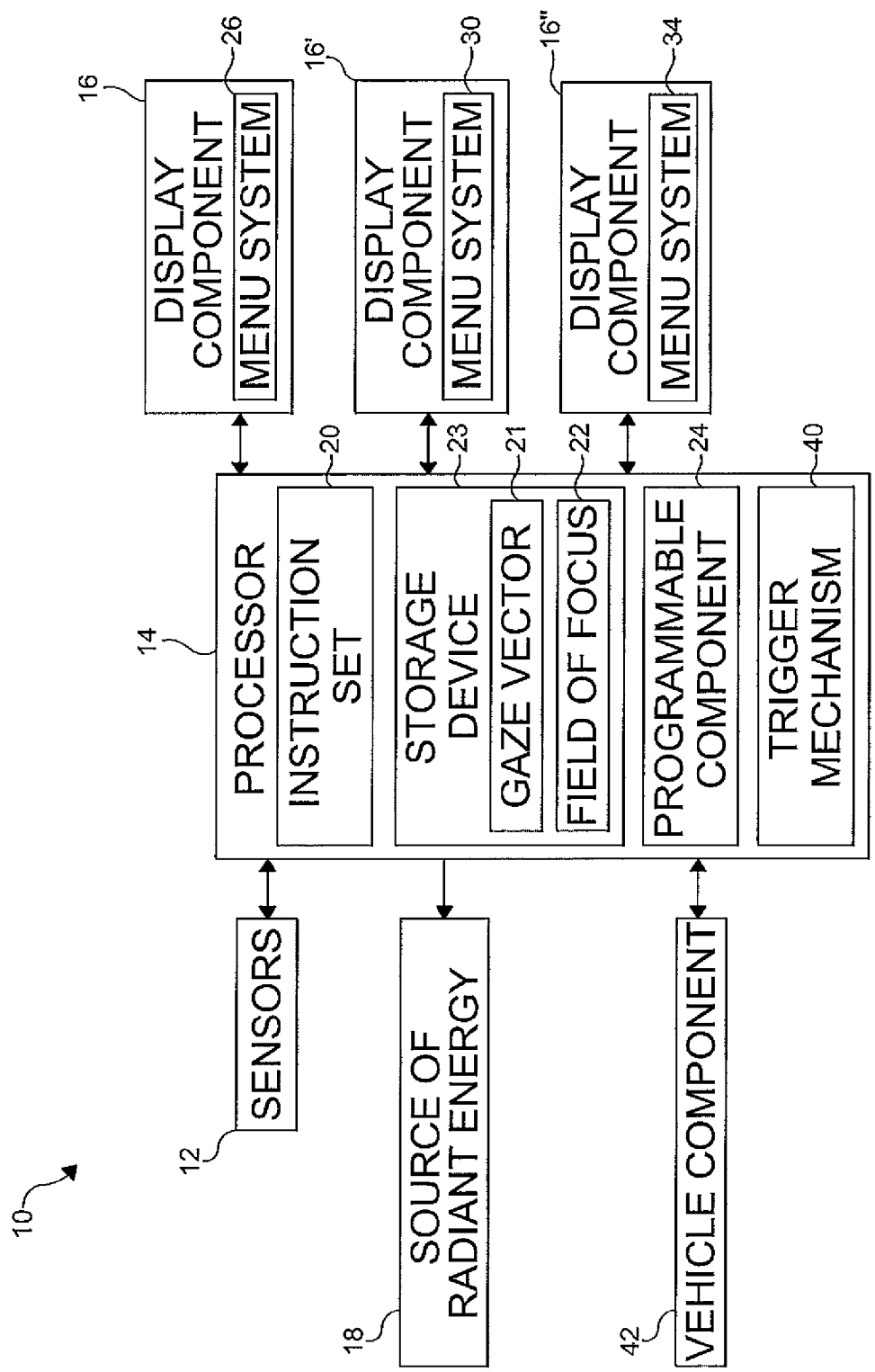
FIG. 2 is a schematic block diagram of the display system of FIG. 1, the display system including a plurality of display components.
Figure 13:
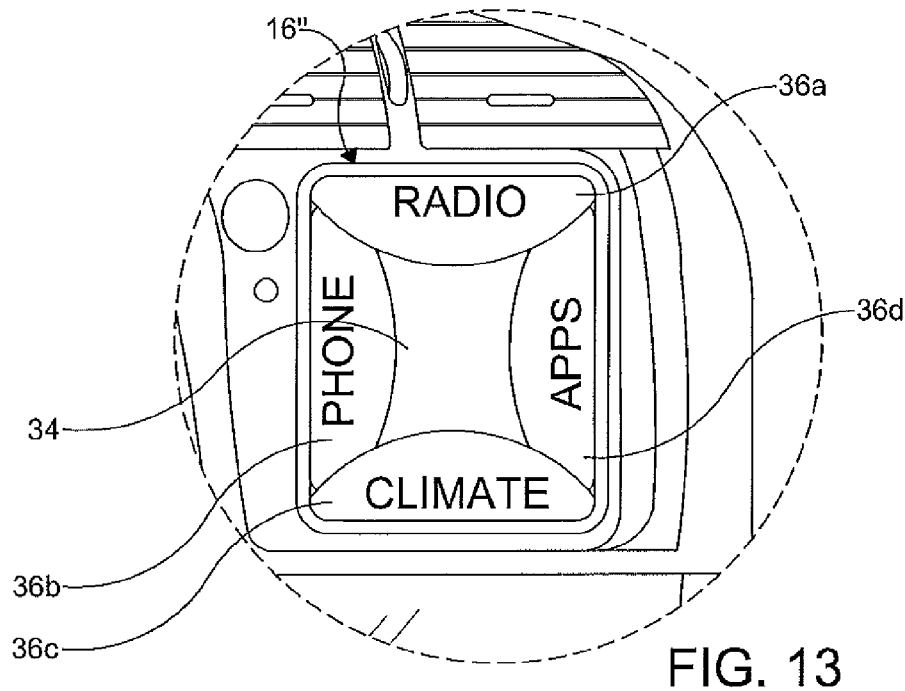
Figure 14:
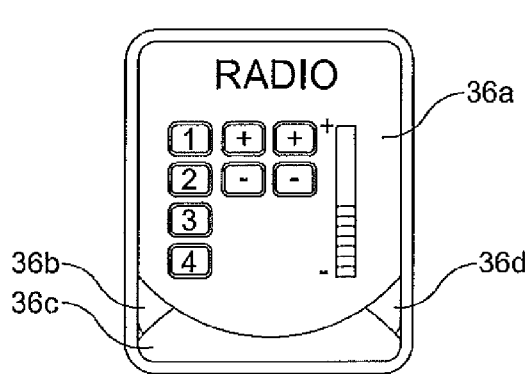
Figure 15:
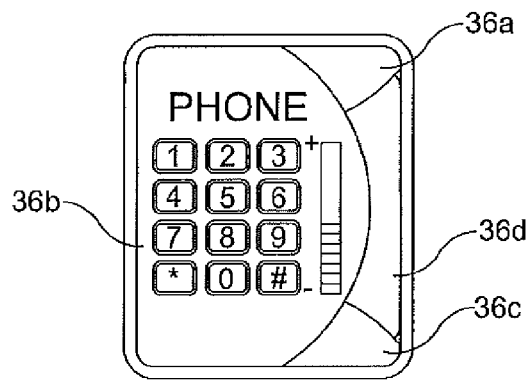
Figure 16:
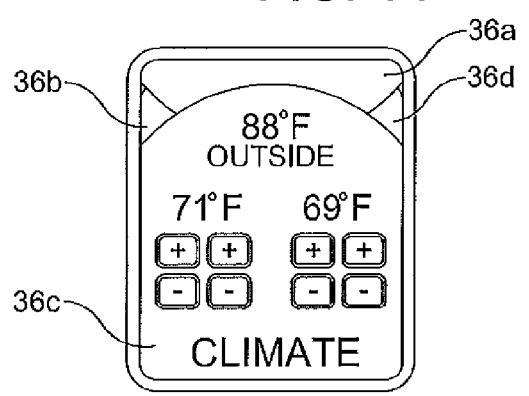
Figure 17:
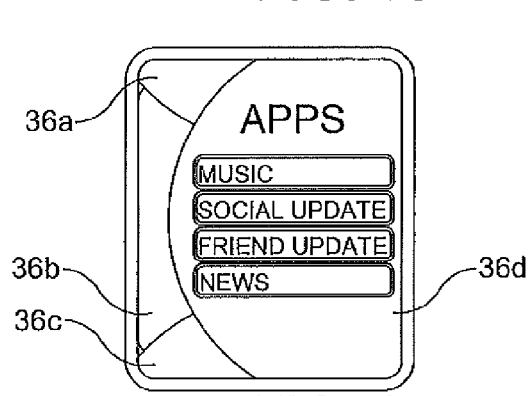
Figure 18:
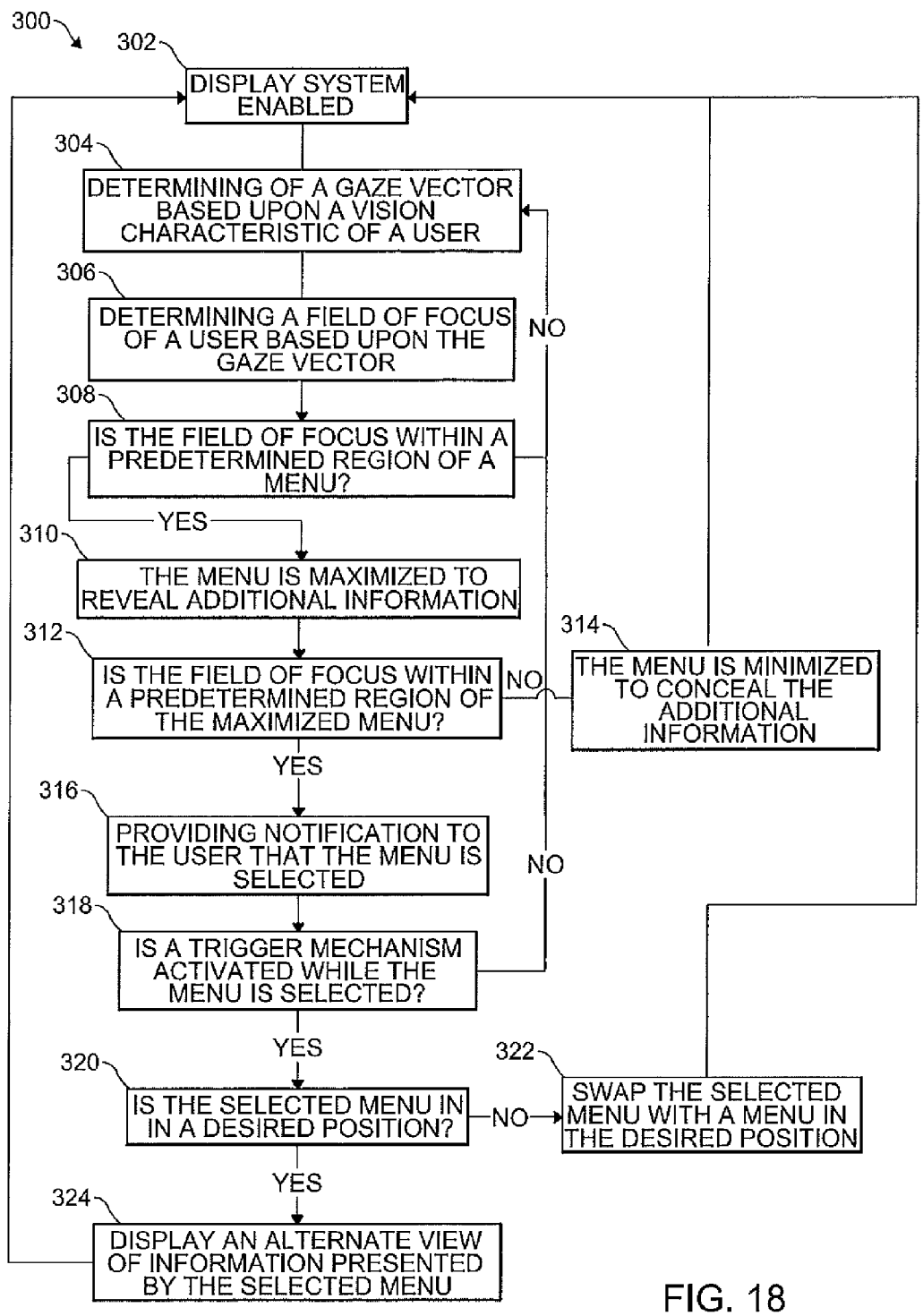
Figure 19:
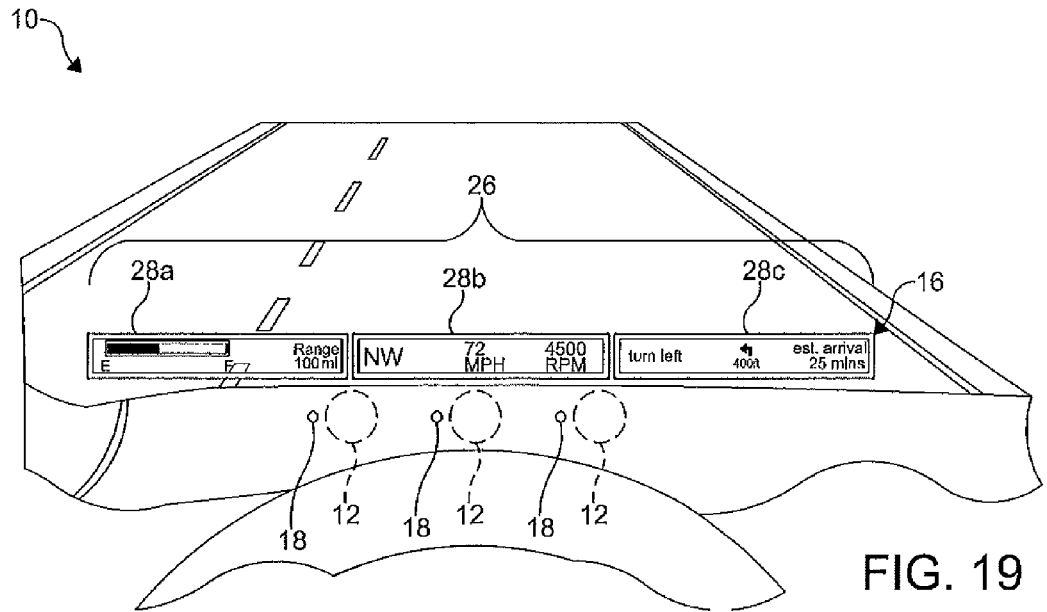
Figure 20:
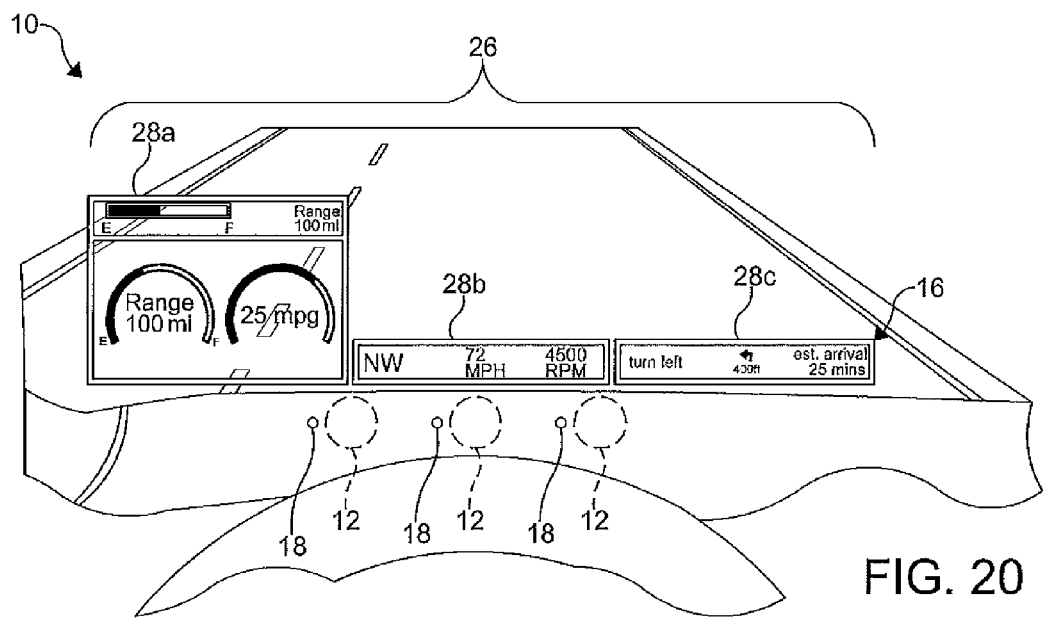
Figure 21:
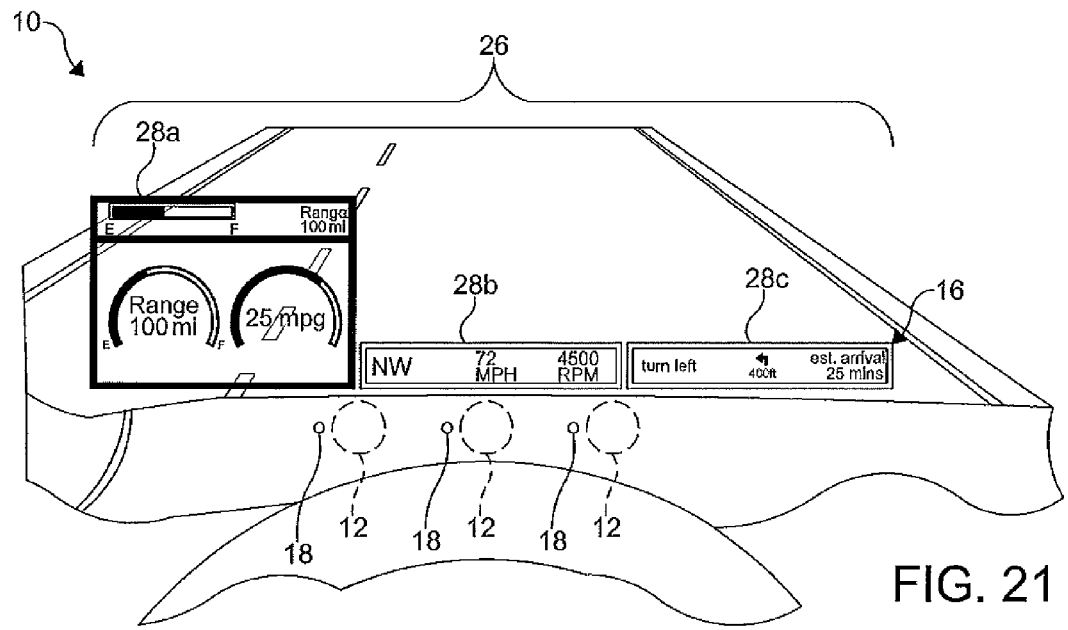
Figure 22:
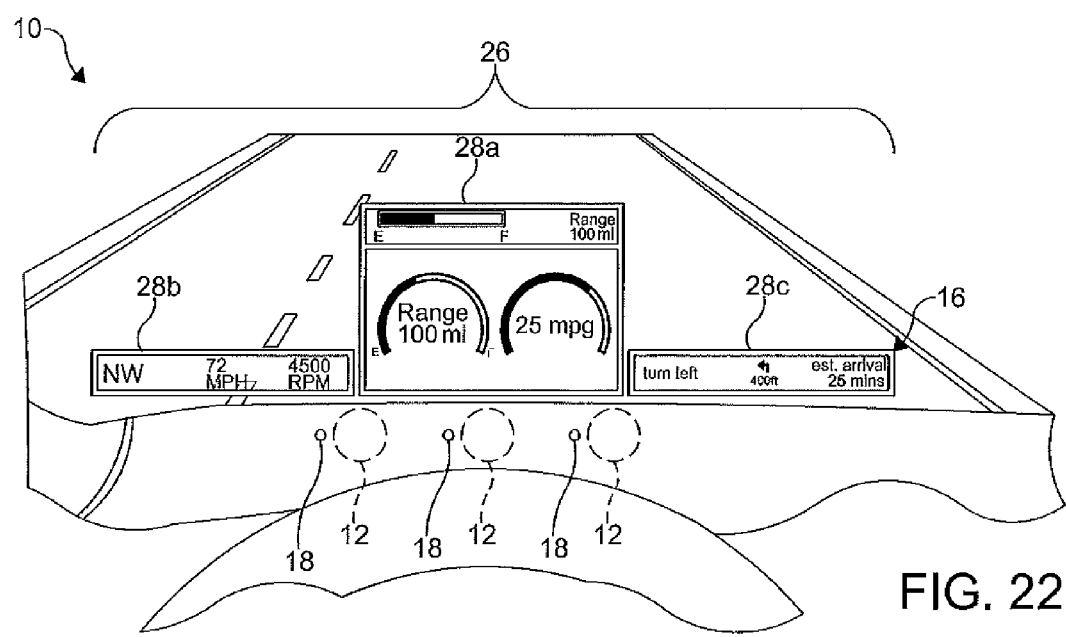
Figure 23:
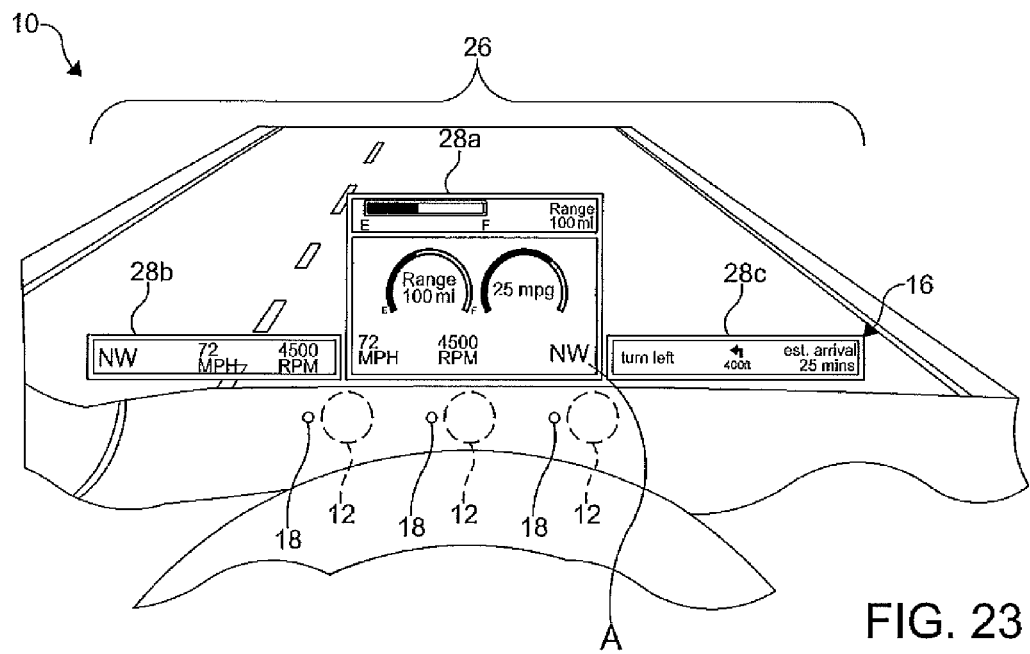

1 depicted in circle 12, wherein the second menu of the display component is maximized and the first and third menus of the display component are minimized;

FIG. 13 is an enlarged fragmentary elevational view of the display component of the display system of FIG. 1 depicted in circle 13, wherein each of a first menu, a second menu, a third menu, and a fourth menu of the display component is minimized;

FIG. 14 is an enlarged elevational view of a menu system of the display component of the display system of FIG. 1 depicted in circle 14, wherein the first menu is maximized and the second, third, and fourth menus are minimized;

FIG. 15 is an enlarged elevational view of the menu system of the display component of the display system of FIG. 1 depicted in circle 15, wherein the second menu is maximized and the first, third, and fourth menus are minimized;

FIG. 16 is an enlarged elevational view of the menu system of the display component of the display system of FIG. 1 depicted in circle 16, wherein the third menu is maximized and the first, second, and fourth menus are minimized;

FIG. 17 is an enlarged elevational view of the menu system of the display component of the display system of FIG. 1 depicted in circle 17, wherein the fourth menu is maximized and the first, second, and third menus are minimized;

FIG. 18 is schematic block diagram of a method of controlling a menu system of at least one of the display components of FIGS. 1-2 according to another embodiment of the invention;

FIG. 19 is an enlarged fragmentary schematic perspective view of the display component of the display system of FIG. 1 depicted in circle 19, wherein each of the first menu, the second menu, and the third menu of the display component is minimized;

FIG. 20 is an enlarged fragmentary schematic perspective view of the display component of the display system of FIG. 1 depicted in circle 20, wherein the first menu of the display component is maximized and the second and third menus of the display component are maximized;

FIG. 21 is an enlarged fragmentary schematic perspective view of the display component of the display system of FIG. 1 depicted in circle 21, wherein the first menu of the display component is selected and in a leftward position;

FIG. 22 is an enlarged fragmentary schematic perspective view of the display component of the display system of FIG. 1 depicted in circle 22, wherein the first menu of the display component is in the center position;

FIG. 23 is an enlarged fragmentary schematic perspective view of the display component of the display system of FIG. 1 depicted in circle 23, wherein an alternate view of the first menu of the display component is displayed in the center position.

DETAILED DESCRIPTION OF EXEMPLARY EMBODIMENTS OF THE INVENTION

The following detailed description and appended drawings describe and illustrate various embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

FIGS. 1-2 illustrate an adaptive display system 10 for a vehicle 11 according to an embodiment of the present invention. As shown, the display system 10 includes at least one sensor 12, a processor 14, and a plurality of adaptive display components 16, 16', 16". The display system 10 can include any number of components and sub-components, as desired. The display system 10 can be integrated in any user environment.

As shown, the at least one sensor 12 is a user tracking device capable of detecting a vision characteristic of a face or head of a user (e.g. a head pose, a gaze vector or direction, a facial feature, and the like). In certain embodiments, the at least one sensor 12 is a complementary metal-oxide-semiconductor (CMOS) camera for capturing an image of at least a portion of a head (e.g. face or eyes) of the user and generating a sensor signal representing the image. However, other cameras, image capturing devices, and the like can be used.

In the embodiment shown, a plurality of the sensors 12 is disposed along a common axis (not shown) to enable an accurate detection of a vision characteristic of the user from multiple viewing angles. However, it is understood that the sensor(s) 12 can be positioned in any location and configuration.

As a non-limiting example, a source of radiant energy 18 is disposed to illuminate at least a portion of a head of the user. As a further non-limiting example, the source of radiant energy 18 may be an infra-red light emitting diode. However, other sources of the radiant energy can be used.

The processor 14 may be any device or system configured to receive an input signal (e.g. the sensor signal), analyze the input signal, and configure at least one of the display components 16, 16', 16" in response to the analysis of the input signal. In certain embodiments, the processor 14 is a microcomputer. In the embodiment shown, the processor 14 receives the input signal from at least one of the sensors 12.

As shown, the processor 14 analyzes the input signal based upon an instruction set 20. The instruction set 20, which may be embodied within any computer readable medium, includes processor executable instructions for configuring the processor 14 to perform a variety of tasks. The processor 14 may execute a variety functions such as controlling the operation of the sensor 12, the display components 16, 16', 16", and other vehicle components 42 (e.g. a sensor, a human machine interface, a microphone, a climate control system, a navigation system, a fuel system, an entertainment system, a steering system, etc.), for example. It is understood that various algorithms and software can be used to analyze an image of a head, a face, or an eye of a user to determine the vision characteristics thereof (e.g. the "Smart Eye" software produced by Smart Eye AB in Sweden). It is further understood that any software or algorithm can be used to detect the vision characteristics of the head/face of the user such as the techniques described in U.S. Pat. Nos. 4,648,052, 4,720,189, 4,836,670, 4,950,069, 5,008,946 and 5,305,012, for example.

As a non-limiting example, the instruction set 20 is a software configured to determine a gaze vector 21 of a user based upon the information received by the processor 14 (e.g. via the sensor signal). As a further non-limiting example, the processor 14 determines a field of focus 22 of at least one of the eyes of a user, wherein a field of focus 22 is a pre-determined portion of a complete field of view of the user. In certain embodiments, the field of focus 22 is defined by a pre-determined range of degrees (e.g. +/– five degrees) from the gaze vector 21 calculated in response to the instruction set 20. It is understood that any range of degrees relative to the calculated gaze vector 21 can be used to define the field of focus 22. It is further understood that other vision characteristics can be determined such as head pose, for example.

In certain embodiments, the processor 14 includes a storage device 23. The storage device 23 may be a single storage device or may be multiple storage devices. Furthermore, the storage device 23 may be a solid state storage system, a magnetic storage system, an optical storage system or any other suitable storage system or device. It is understood that the storage device 23 may be configured to store the instruction set 20. Other data and information may be stored and cataloged in the storage device 23 such as the data collected by the sensor 12, the calculated gaze vector 21, and the field of focus 22, for example.

The processor 14 may further include a programmable component 24. It is understood that the programmable component 24 may be in communication with any other component of the display system 10 such as the sensor 12 and the user interface 16, for example. In certain embodiments, the programmable component 24 is configured to manage and control processing functions of the processor 14. Specifically, the programmable component 24 is configured to modify the instruction set 20 and control the analysis of the signals and information received by the processor 14. It is understood that the programmable component 24 may be configured to manage and control the sensor 12 and at least one of the display components 16, 16', 16". It is further understood that the programmable component 24 may be configured to store data and information on the storage device 23, and retrieve data and information from the storage device 23.

The display component 16 shown is a heads-up-display (HUD). The display component 16 is configured to generate a visual output to the user. As a non-limiting example, the visual output generated is a menu system 26. The menu system 26 shown includes a first menu 28a, a second menu 28b, and a third menu 28c arranged along a common axis (not shown). Information displayed by each of the menus 28a, 28b, 28c is based upon at least one predetermined user preference. User preferences include, but are not limited to a speedometer reading, a compass reading, a tachometer reading, a fuel level sensor reading, a distance range based on the fuel level, a navigation system feature, a climate control system feature, and an entertainment system feature. It is understood that any number of the menus can be employed as desired.

The display component 16' shown is a dashboard display. The display component 16' is configured to generate a visual output to the user. As a non-limiting example, the visual output generated is a menu system 30. The menu system 30 shown includes a first menu 32a, a second menu 32b, and a third menu 32c arranged along a common axis (not shown). Information displayed by each of the menus 32a, 32b, 32c is based upon at least one predetermined user preference. User preferences include, but are not limited to a speedometer reading, a compass reading, a tachometer reading, a fuel level sensor reading, a distance range based on the fuel level, a navigation system feature, a climate control system feature, and an entertainment system feature. It is understood that any number of the menus can be employed as desired.

The display component 16" is a center stack display. The display component 16" is configured to generate a visual output to the user. As a non-limiting example, the visual output generated is a menu system 34. The menu system 34 shown includes a first menu 36a, a second menu 36b, a third menu 36c, and a fourth menu 36d. Each of the menus 36a, 36b, 36c, 36d is arranged a respective side of the center stack display. Information displayed by each of the menus 36a, 36b, 36c, 36d is based upon at least one predetermined user preference. User preferences include, but are not limited to a speedometer reading, a compass reading, a tachometer reading, a fuel level sensor reading, a distance range based on the fuel level, a navigation system feature, a climate control system feature, and an entertainment system feature. It is understood that any number of the menus can be employed as desired.

In operation, the user interacts with the display components 16, 16', 16" of the display system 10 in a manner described in detail hereinafter. The processor 14 continuously receives the input signals (e.g. sensor signal) and information relating to the vision characteristics of the user. The processor 14 analyzes the input signal and the information based upon the instruction set 20 to determine the vision characteristics of the user. At least one of the display components 16, 16', 16" is configured by the processor 14 based upon the vision characteristics of the user. As a non-limiting example, the processor 14 transmits a control signal to at least one of the display components 16, 16', 16" to modify the visible output generated based upon the vision characteristic of the user.

Figure 3:
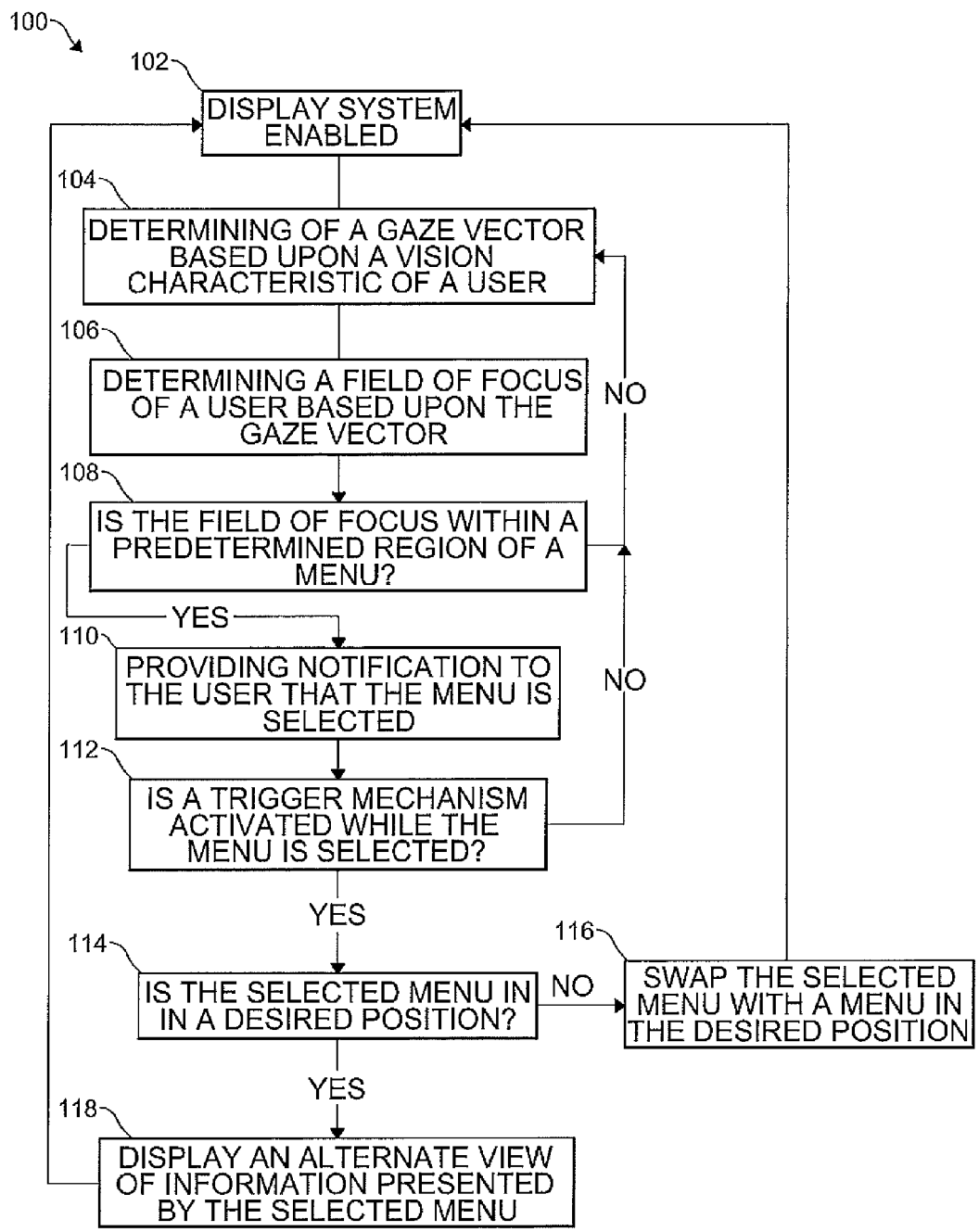
FIG. 3 is a schematic block diagram of a method of controlling a menu system of at least one of the display components of FIGS. 1-2 according to an embodiment of the invention.

FIG. 3 illustrates a method 100 of controlling each of the menu systems 26, 30, 34 of the display components 16, 16', 16" according to one embodiment of the invention. The method 100 of controlling the menu system 26 is substantially similar to the method 100 of controlling the menu systems 30, 34. Therefore, for simplicity, only the method 100 of controlling the menu system 26 will be described hereinafter. In step 102, the display system 10 is enabled.

In step 104, the processor 14 receives a signal from each of the sensors 12 and determines a gaze vector 21 based upon a vision characteristic of a user. As a non-limiting example, the processor 14 determines the gaze vector 21 based upon the instruction set 20. In step 106, the processor 14 calculates a field of focus 22 of the user based upon the gaze vector 21. As a non-limiting example, the processor 14 determines the gaze vector 21 based upon the instruction set 20.

In step 108, the processor 14 analyzes the field of focus 22 of the user and determines whether the field of focus 22 is within a predetermined region of one of the menus 28a, 28b, 28c of the menu system 26. As a non-limiting example, the processor 14 determines whether the field of focus 22 is within the predetermined region of one of the menus 28a, 28b, 28c based upon the instruction set 20. When the field of focus 22 is outside the predetermined regions of the menus 28a, 28b, 28c, step 104 is repeated. When the field of focus 22 is within the predetermined region of one of the menus 28a, 28b, 28c, in step 110, the processor 14 controls the display component 16 to provide notification to the user that one of the menus 28a, 28b, 28c is selected. It is understood that notification can be by any means as desired such as a visual notification (e.g. highlighting the menu selected), an audible notification (e.g. noise alert), or a haptic notification (e.g. vibration), for example. In a non-limiting example, the processor 14 controls the display component 16 or other vehicle component 42 (e.g. a steering wheel, an entertainment system, a horn, etc.) based upon the instruction set 20 to provide the notification to the user.

In step 112, the processor 14 determines whether a trigger mechanism 40 is activated by the user while the one of the menus 28a, 28b, 28c is selected. It is understood that trigger mechanism 40 can be any trigger mechanism 40 activated by any means such as a spatial command (e.g. an eye, a head, or hand movement), an audible command (e.g. a voice instruction), and a haptic command (e.g. a push button, a switch, a slide, etc.), for example. In certain embodiments, the processor 14 receives a signal from at least one vehicle component 42 (e.g. a sensor, a human machine interface, a microphone, etc.) for activation of the trigger mechanism 40. In a non-limiting example, the processor 14 determines activation of the trigger mechanism 40 based upon the instruction set 20.

When the trigger mechanism 40 is not activated while the one of the menus 28a, 28b, 28c is selected, step 104 is repeated.

When the trigger mechanism 40 is activated while the one of the menus 28a, 28b, 28c is selected, in step 114, the processor 14 determines whether the selected one of the menus 28a, 28b, 28c is in a desired position. For example, in the embodiment shown, the desired position is a center position. However, it is understood that the desired position may be other positions in other configurations of the menus such as a central position in a circular configuration of five menus, a top position in a vertically linear configuration of the menus, an upper left position in a rectangular configuration of at least four menus, and the like, for example. In a non-limiting example, the processor 14 determines the position of the selected one of the menus 28a, 28b, 28c based upon the instruction set 20. When the selected one of the menus 28a, 28b, 28c is not in the desired position, in step 116, the processor 14 controls the display component 16 and swaps the selected one of the menus 28a, 28b, 28c with the one of the menus 28a, 28b, 28c in the desired position. Once the selected one of the menus 28a, 28b, 28c is in the desired position, the step 102 is repeated. When the selected one of the menus 28a, 28b, 28c is in the desired position, in step 118, the processor 14 controls the display component 16 to display an alternate view A of information presented by the selected one of the menus 28a, 28b, 28c. Once the selected one of the menus 28a, 28b, 28c is in the desired position, the step 102 is repeated.

Figure 4:
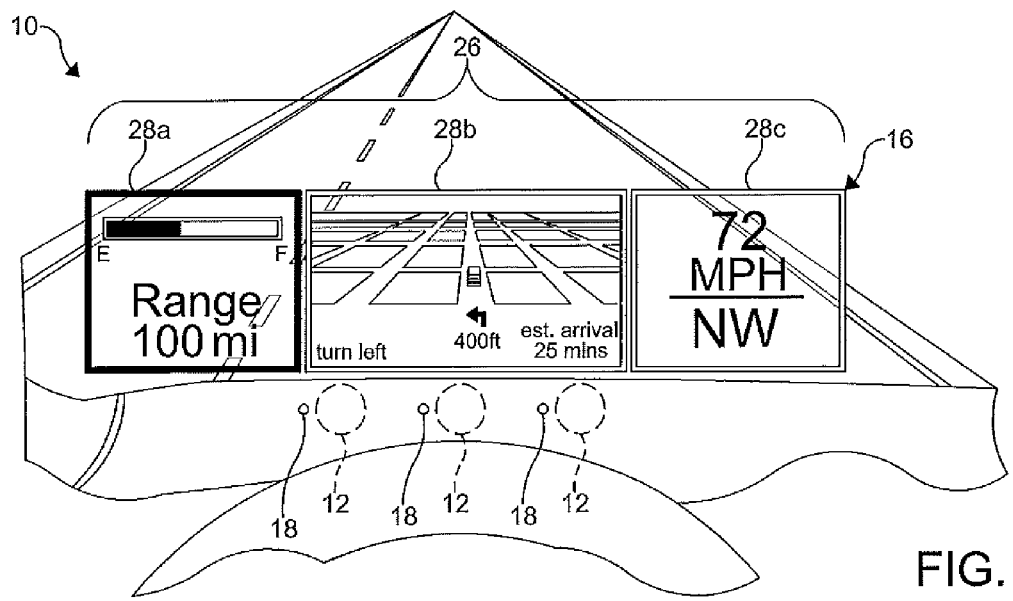
FIG. 4 is an enlarged fragmentary schematic perspective view of the display component of the display system of FIG. 1 depicted in circle 4, wherein a first menu of the display component is selected and in a leftward position.

An example of the method 100 of FIG. 3 is illustrated in FIGS. 4-7. As shown in FIG. 4, the user is gazing toward the first menu 28a of the menu system 26 of the display component 16, wherein a field of focus 22 of the gaze vector 21 of the user is determined by the processor 14 to be within the predetermined region of the first menu 28a. Accordingly, notification is provided to the user that the first menu 28a is selected.

Figure 5:
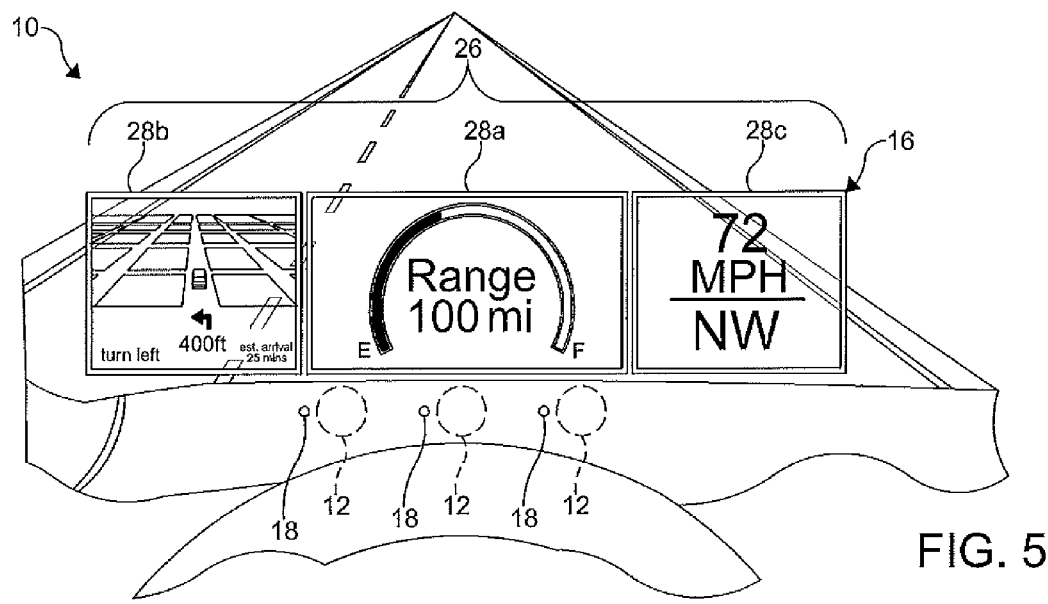
FIG. 5 is an enlarged fragmentary schematic perspective view of the display component of the display system of FIG. 1 depicted in circle 5, wherein the first menu of the display component is in a center position.

As shown in FIG. 5, the trigger mechanism 40 has been activated while the first menu 28a was selected. Accordingly, the selected first menu 28a is in the center position and the second menu 28b is in the leftward position.

Figure 6:
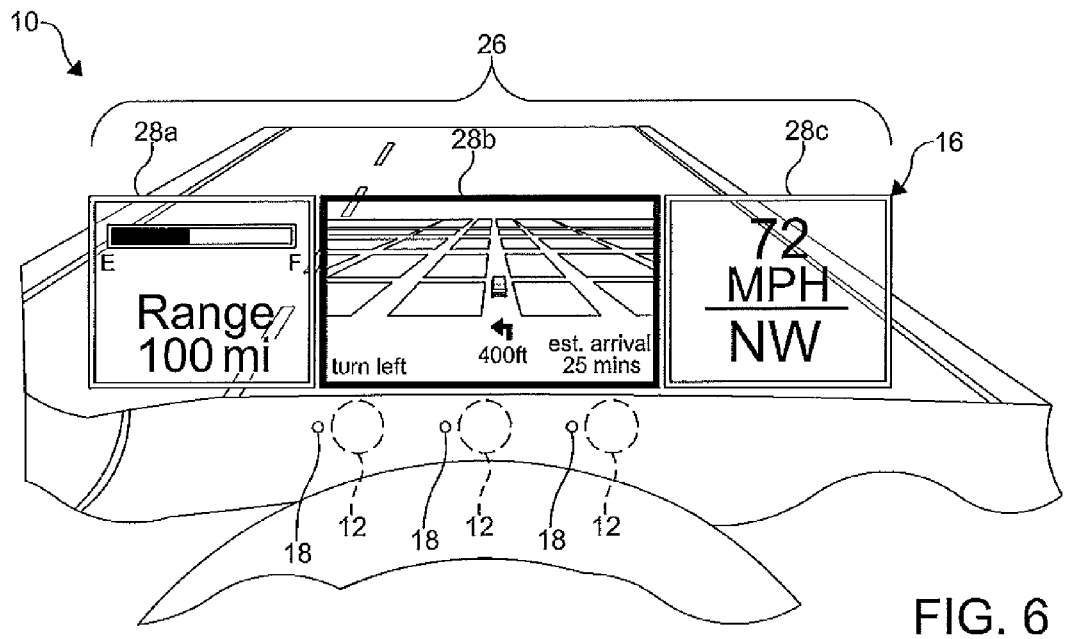
FIG. 6 is an enlarged fragmentary schematic perspective view of the display component of the display system of FIG. 1 depicted in circle 6, wherein a second menu of the display component is selected and in the center position.

As shown in FIG. 6, a field of focus 22 of the gaze vector 21 of the user is determined by the processor 14 to be within the predetermined region of the second menu 28b of the menu system 26. Accordingly, notification is provided to the user that the second menu 28b is selected.

Figure 7:
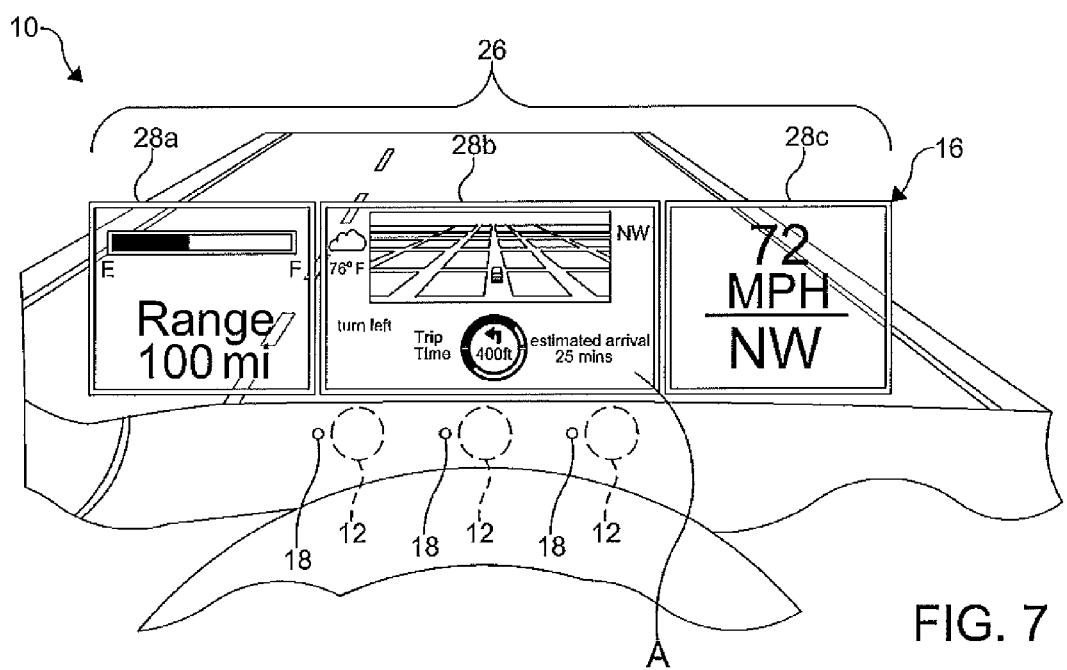
FIG. 7 is an enlarged fragmentary schematic perspective view of the display component of the display system of FIG. 1 depicted in circle 7, wherein an alternate view of the second menu of the display component is displayed in the center position.

As shown in FIG. 7, the trigger mechanism 40 has been activated while the second menu 28b was selected. Since the second menu 28b is in the center position, the processor 14 controls the display component 16 to display an alternate view A of the information presented by the selected second menu 28b.

Figure 8:
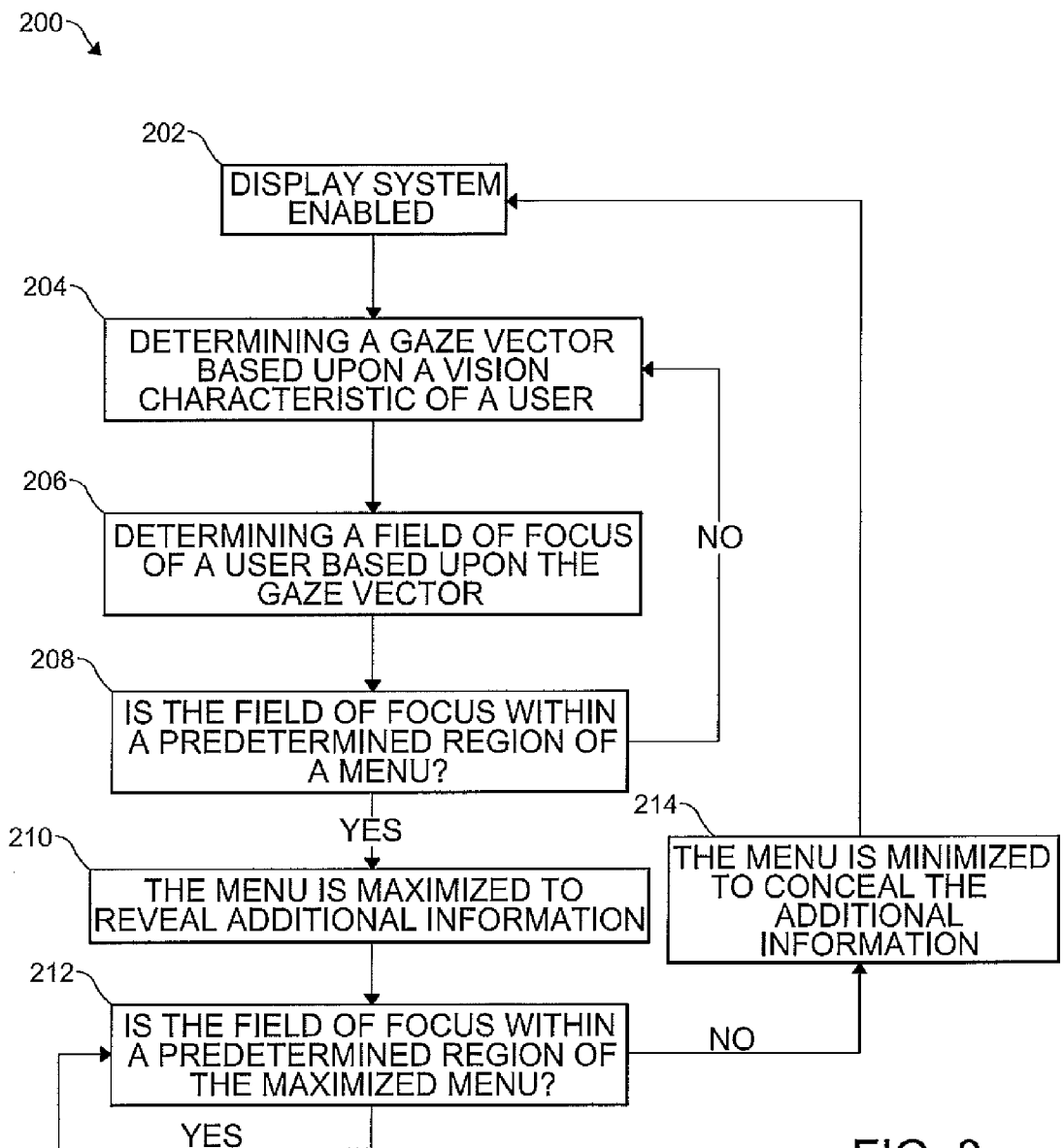
FIG. 8 is schematic block diagram of a method of controlling a menu system of at least one of the display components of FIGS. 1-2 according to another embodiment of the invention.

FIG. 8 illustrates a method 200 of controlling each of the menu systems 26, 30, 34 of the display components 16, 16', 16" according to another embodiment of the invention. The method 200 of controlling the menu system 26 is substantially similar to the method 200 of controlling the menu systems 30, 34. Therefore, for simplicity, only the method 200 of controlling the menu system 26 will be described hereinafter. In step 202, the display system 10 is enabled.

In step 204, the processor 14 receives a signal from each of the sensors 12 and determines a gaze vector 21 based upon a vision characteristic of a user. As a non-limiting example, the processor 14 determines the gaze vector 21 based upon the instruction set 20. In step 206, the processor 14 calculates a field of focus 22 of the user based upon the gaze vector 21. As a non-limiting example, the processor 14 determines the gaze vector 21 based upon the instruction set 20.

In step 208, the processor 14 analyzes the field of focus 22 of the user and determines whether the field of focus 22 is within a predetermined region of one of the menus 28a, 28b, 28c of the menu system 26. As a non-limiting example, the processor 14 determines whether the field of focus 22 is within the predetermined region of one of the menus 28a, 28b, 28c based upon the instruction set 20. When the field of focus 22 is outside the predetermined regions of the menus 28a, 28b, 28c, step 204 is repeated. When the field of focus 22 is within the predetermined region of one of the menus 28a, 28b, 28c, in step 210, the processor 14 controls the display component 16 to expand the one of the menus 28a, 28b, 28c from a minimized position to a maximized position and reveal additional information. In a non-limiting example, the processor 14 controls the display component 16 based upon the instruction set 20 to expand the one of the menus 28a, 28b, 28c.

In step 212, the processor 14 analyzes the field of focus 22 of the user and determines whether the field of focus 22 is within a predetermined region of the maximized menu 28a, 28b, 28c of the menu system 26. As a non-limiting example, the processor 14 determines whether the field of focus 22 is within the predetermined region of the maximized menu 28a, 28b, 28c based upon the instruction set 20. When the field of focus 22 is outside the predetermined regions of the maximized menu 28a, 28b, 28c, in step 214, the maximized menu 28a, 28b, 28c is retracted from the maximized position to the minimized position to conceal the additional information. When the field of focus 22 is within the predetermined region of one of the menus 28a, 28b, 28c, step 212 is repeated.

Figure 9:
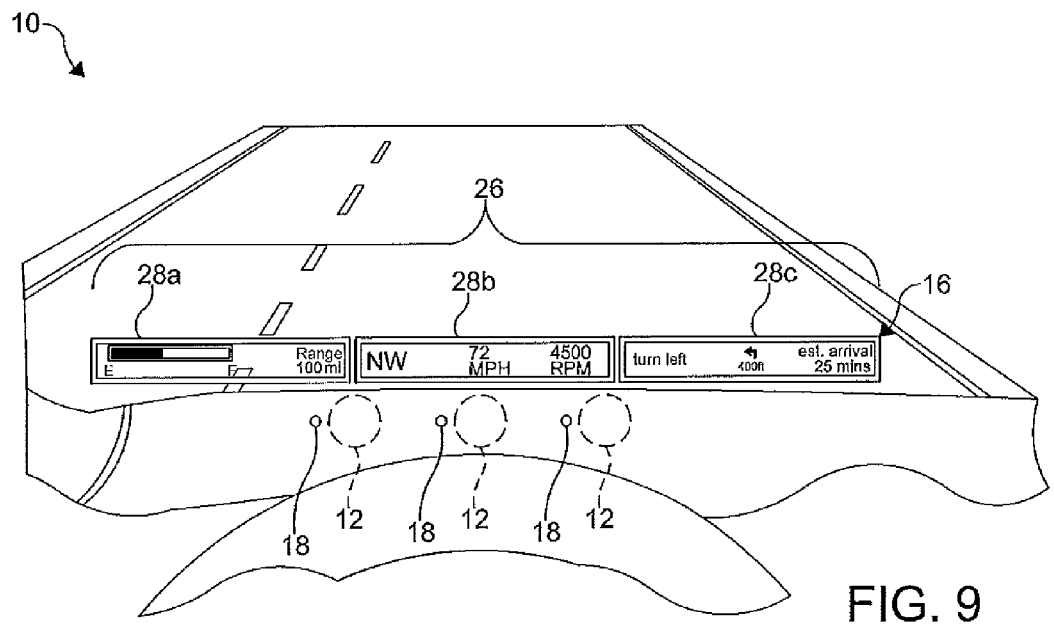
FIG. 9 is an enlarged fragmentary schematic perspective view of the display component of the display system of FIG. 1 depicted in circle 9, wherein each of a first menu, a second menu, and a third menu of the display component is minimized.

An example of the method 200 of FIG. 8 is illustrated in FIGS. 9-17. As shown in FIG. 9, the user is gazing away from the menus 28a, 28b, 28c of the menu system 26 of the display component 16, wherein a field of focus 22 of the gaze vector 21 of the user is determined by the processor 14 to be outside the predetermined region of the menus 28a, 28b, 28c. Accordingly, each of the menus 28a, 28b, 28c of the menu system 26 of the display component 16 is in the minimized position.

Figure 10:
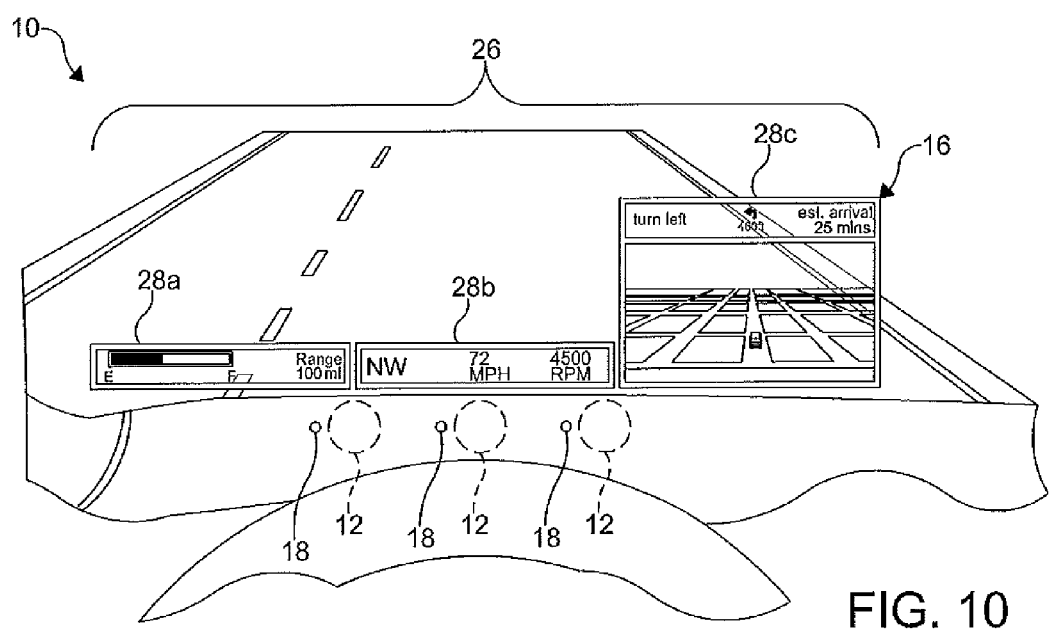
FIG. 10 is an enlarged fragmentary schematic perspective view of the display component of the display system of FIG. 1 depicted in circle 10, wherein the first and second menus of the display component are minimized and the third menu of the display component is maximized.

As shown in FIG. 10, the user is gazing toward the third menu 28c of the menu system 26 of the display component 16, wherein a field of focus 22 of the gaze vector 21 of the user is determined by the processor 14 to be within the predetermined region of the third menu 28c. Accordingly, the third menu 28c is expanded from the minimized position to the maximized position to reveal the additional information and each of the menus 28a, 28b is in the minimized position to conceal the additional information.

Figure 11:
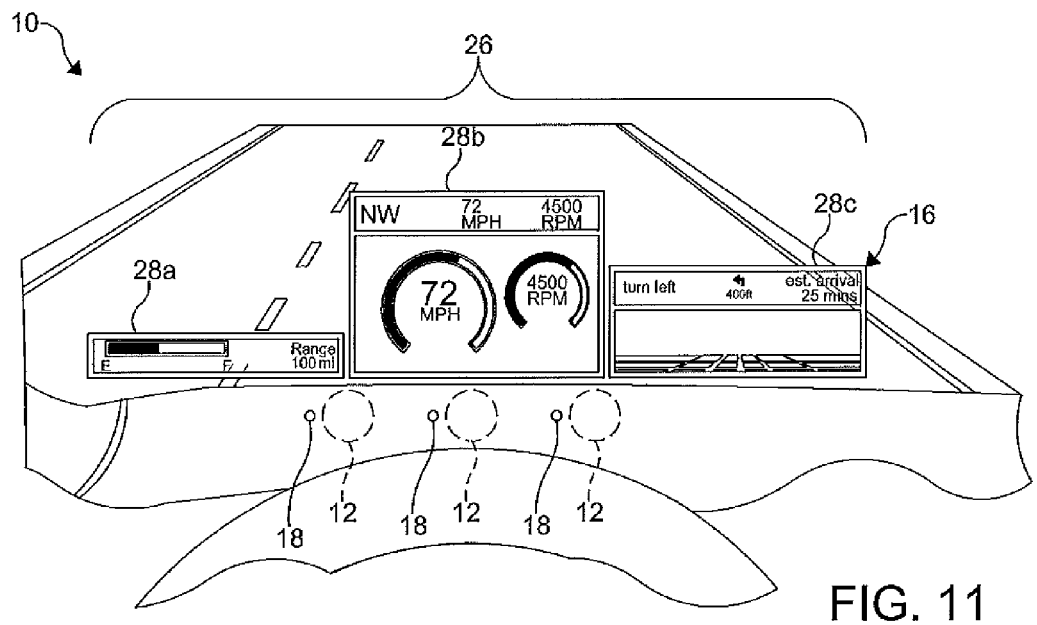
FIG. 11 is an enlarged fragmentary schematic perspective view of the display component of the display system of FIG. 1 depicted in circle 11, showing a transition of a gaze of a user from the third menu of the display component to the second menu of the display component.

As shown in FIG. 11, the transition of the user gaze is from the third menu 28c of the menu system 26 of the display component 16 to the second menu 28b of the menu system 26 of the display component 16, wherein a field of focus 22 of the gaze vector 21 of the user is determined by the processor 14 to be within the predetermined region of the second menu 28b. Accordingly, the second menu 28b is expanded from the minimized position to the maximized position to reveal additional information, the third menu 28c is partially retracted to conceal the additional information, and the first menu 28a is entirely retracted to the minimized position to conceal the additional information.

Figure 12:
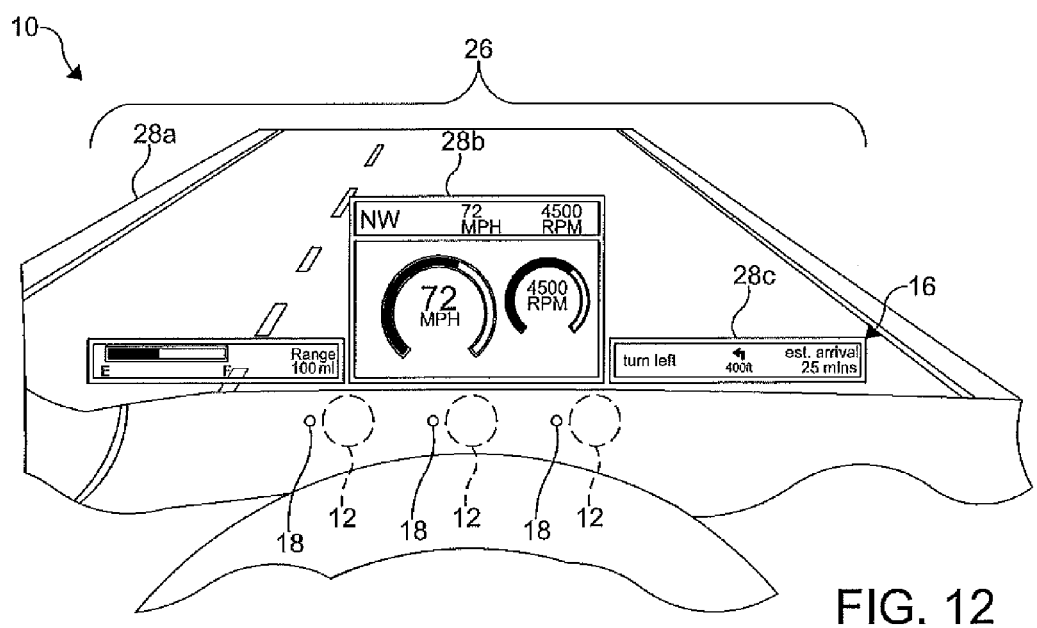
FIG. 12 is an enlarged fragmentary schematic perspective view of the display component of the display system of FIG.

As shown in FIG. 12, the user is gazing toward the second menu 28b of the menu system 26 of the display component 16, wherein a field of focus 22 of the gaze vector 21 of the user is determined by the processor 14 to be within the predetermined region of the second menu 28b. Accordingly, the second menu 28b is expanded from the minimized position to the maximized position to reveal the additional information and each of the menus 28a, 28c is in the minimized position to conceal the additional information.

As shown in FIG. 13, the user is gazing away from the menus 36a, 36b, 36c, 36d of the menu system 34 of the display component 16", wherein a field of focus 22 of the gaze vector 21 of the user is determined by the processor 14 to be outside the predetermined region of the menus 36a, 36b, 36c, 36d. Accordingly, each of the menus 36a, 36b, 36c, 36d of the menu system 34 of the display component 16" is in the minimized position.

As shown in FIG. 14, the user is gazing toward the first menu 36a of the menu system 34 of the display component 16", wherein a field of focus 22 of the gaze vector 21 of the user is determined by the processor 14 to be within the predetermined region of the first menu 36a. Accordingly, the first menu 36a is expanded from the minimized position to the maximized position to reveal the additional information and each of the menus 36b, 36c, 36d is in the minimized position to conceal the additional information.

As shown in FIG. 15, the user is gazing toward the second menu 36b of the menu system 34 of the display component 16", wherein a field of focus 22 of the gaze vector 21 of the user is determined by the processor 14 to be within the predetermined region of the second menu 36b. Accordingly, the second menu 36b is expanded from the minimized position to the maximized position to reveal the additional information and each of the menus 36a, 36c, 36d is in the minimized position to conceal the additional information.

As shown in FIG. 16, the user is gazing toward the third menu 36c of the menu system 34 of the display component 16", wherein a field of focus 22 of the gaze vector 21 of the user is determined by the processor 14 to be within the predetermined region of the third menu 36c. Accordingly, the third menu 36c is expanded from the minimized position to the maximized position to reveal the additional information and each of the menus 36a, 36b, 36d is in the minimized position to conceal the additional information.

As shown in FIG. 17, the user is gazing toward the fourth menu 36d of the menu system 34 of the display component 16", wherein a field of focus 22 of the gaze vector 21 of the user is determined by the processor 14 to be within the predetermined region of the fourth menu 36d. Accordingly, the fourth menu 36d is expanded from the minimized position to the maximized position to reveal the additional information and each of the menus 36a, 36b, 36c is in the minimized position to conceal the additional information.

FIG. 18 illustrates a method 300 of controlling each of the menu systems 26, 30, 34 of the display components 16, 16', 16" according to another embodiment of the invention. The method 300 of controlling the menu system 26 is substantially similar to the method 300 of controlling the menu systems 30, 34. Therefore, for simplicity, only the method 300 of controlling the menu system 26 will be described hereinafter. In step 302, the display system 10 is enabled.

In step 304, the processor 14 receives a signal from each of the sensors 12 and determines a gaze vector 21 based upon a vision characteristic of a user. As a non-limiting example, the processor 14 determines the gaze vector 21 based upon the instruction set 20. In step 306, the processor 14 calculates a field of focus 22 of the user based upon the gaze vector 21. As a non-limiting example, the processor 14 determines the gaze vector 21 based upon the instruction set 20.

In step 308, the processor 14 analyzes the field of focus 22 of the user and determines whether the field of focus 22 is within a predetermined region of one of the menus 28a, 28b, 28c of the menu system 26. As a non-limiting example, the processor 14 determines whether the field of focus 22 is within the predetermined region of one of the menus 28a, 28b, 28c based upon the instruction set 20. When the field of focus 22 is outside the predetermined regions of the menus 28a, 28b, 28c, step 304 is repeated.

When the field of focus 22 is within the predetermined region of one of the menus 28a, 28b, 28c, in step 310, the processor 14 controls the display component 16 to expanded the one of the menus 28a, 28b, 28c from the minimized position to the maximized position and reveal additional information. In a non-limiting example, the processor 14 controls the display component 16 based upon the instruction set 20 to expand the one of the menus 28a, 28b, 28c.

In step 312, the processor 14 analyzes the field of focus 22 of the user and determines whether the field of focus 22 is within a predetermined region of the maximized menu 28a, 28b, 28c of the menu system 26. As a non-limiting example, the processor 14 determines whether the field of focus 22 is within the predetermined region of the maximized menu 28a, 28b, 28c based upon the instruction set 20. When the field of focus 22 is outside the predetermined regions of the maximized menu 28a, 28b, 28c, in step 314, the maximized menu 28a, 28b, 28c is retracted from the maximized position to the minimized position to conceal the additional information. When the field of focus 22 is within the predetermined region of the maximized menu 28a, 28b, 28c, in step 316, the processor 14 controls the display component 16 to provide notification to the user that the maximized menu 28a, 28b, 28c is selected. It is understood that notification can be by any means as desired such as a visual notification (e.g. highlighting the menu selected), an audible notification (e.g. noise alert), or a haptic notification (e.g. vibration), for example. In a non-limiting example, the processor 14 controls the display component 16 or other vehicle component 42 (e.g. a steering wheel, an entertainment system, a horn, etc.) based upon the instruction set 20 to provide the notification to the user.

In step 318, the processor 14 determines whether a trigger mechanism 40 is activated by the user while the maximized menu 28a, 28b, 28c is selected. It is understood that trigger mechanism 40 can be any trigger mechanism 40 activated by any means such as a spatial command (e.g. an eye, a head, or hand movement), an audible command (e.g. a voice instruction), and a haptic command (e.g. a push button, a switch, a slide, etc.), for example. In certain embodiments, the processor 14 receives a signal from at least one vehicle component 42 (e.g. a sensor, a human machine interface, a microphone, etc.) for activation of the trigger mechanism 40. In a non-limiting example, the processor 14 determines activation of the trigger mechanism 40 based upon the instruction set 20. When the trigger mechanism 40 is not activated while the maximized menu 28a, 28b, 28c is selected, step 304 is repeated.

When the trigger mechanism 40 is activated while the one of the menus 28a, 28b, 28c is selected, in step 320, the processor 14 determines whether the selected maximized menu 28a, 28b, 28c is in a desired position. For example, in the embodiment shown, the desired position is a center position. However, it is understood that the desired position may be other positions in other configurations of the menus such as a central position in a circular configuration of five menus, a top position in a vertically linear configuration of the menus, an upper left position in a rectangular configuration of at least four menus, and the like, for example. In a non-limiting example, the processor 14 determines the position of the selected maximized menu 28a, 28b, 28c based upon the instruction set 20. When the selected maximized menu 28a, 28b, 28c is not in the desired position, in step 322, the processor 14 controls the display component 16 and swaps the selected maximized menu 28a, 28b, 28c with the one of the menus 28a, 28b, 28c in the desired position. Once the selected maximized menu 28a, 28b, 28c is in the desired position, the step 302 is repeated. When the selected maximized menu 28a, 28b, 28c is in the desired position, in step 324, the processor 14 controls the display component 16 to display an alternate view of information presented by the selected maximized menu 28a, 28b, 28c. Once the selected maximized menu 28a, 28b, 28c is in the desired position, the step 302 is repeated.

An example of the method 300 of FIG. 18 is illustrated in FIGS. 19-23. As shown in FIG. 19, the user is gazing away from the menus 28a, 28b, 28c of the menu system 26 of the display component 16, wherein a field of focus 22 of the gaze vector 21 of the user is determined by the processor 14 to be outside the predetermined region of the menus 28a, 28b, 28c. Accordingly, each of the menus 28a, 28b, 28c of the menu system 26 of the display component 16 is in the minimized position.

As shown in FIG. 20, the user is gazing toward the first menu 28a of the menu system 26 of the display component 16, wherein a field of focus 22 of the gaze vector 21 of the user is determined by the processor 14 to be within the predetermined region of the first menu 28a. Accordingly, the first menu 28a is expanded from the minimized position to the maximized position to reveal the additional information and each of the menus 28b, 28c is in the minimized position to conceal the additional information.

As shown in FIG. 21, a field of focus 22 of the gaze vector 21 of the user is determined by the processor 14 to be within the predetermined region of the maximized first menu 28a. Accordingly, notification is provided to the user that the maximized first menu 28a is selected.

As shown in FIG. 22, the trigger mechanism 40 has been activated while the maximized first menu 28a was selected. Accordingly, the selected maximized first menu 28a is swapped to the center position, and each of the menus 28b, 28c is in the minimized position.

As shown in FIG. 23, the trigger mechanism 40 has been activated while the selected maximized first menu 28a was in the center position. Accordingly, the processor 14 controls the display component 16 to display an alternate view A of the information presented by the selected maximized first menu 28a.

From the foregoing description, one ordinarily skilled in the art can easily ascertain the essential characteristics of this invention and, without departing from the spirit and scope thereof, make various changes and modifications to the invention to adapt it to various usages and conditions.

What is claimed is:

1. A method of controlling a display component of a display system of a vehicle, the method comprising the steps of:
   providing the display component configured to present a menu system to a user, wherein the display component is a heads-up-display and the menu system includes a plurality of menus arranged along a common axis;
   providing a sensor to continuously detect a vision characteristic of a user;
   determining a field of focus of a user based upon the vision characteristic;
   determining the field of focus of the user is in a predetermined region of one of the menus of the menu system and selecting the one of the menus of the menu system;
   controlling a configuration of the selected menu automatically based only upon a current position of the field of focus by
      expanding the selected menu of the menu system from a minimized position to a maximized position revealing additional information,
      swapping the maximized selected menu of the menu system with another menu of the menu system in a desired position,
      wherein the swapping results in the selected menu of the menu system being moved to a center position of the menu system, and
      activating a trigger mechanism while the field of focus of the user is in the predetermined region of the maximized selected menu in the center position of the menu system, and
      displaying an alternate view of the information presented by the maximized selected menu in the center position of the menu system.

2. The method according to claim 1, wherein the configuration of the selected menu includes at least one of a view of information presented by the selected menu and a position of the selected menu.

3. The method according to claim 1, further comprising the step of providing a processor in communication with the sensor and the display component,
   wherein the processor receives a signal from the sensor, analyzes the signal from the sensor based upon an instruction set to determine the vision characteristic of the user.

4. The method according to claim 3, wherein the instruction set is a software for determining at least one of a head pose of the user, a gaze direction of the user, and a field of focus of the user.

5. The method according to claim 1, further comprising the step of providing a source of radiant energy to illuminate a portion of the user to facilitate the detecting of the vision characteristic of the user.

6. The method according to claim 1, further comprising the step of providing notification to the user when the field of focus of the user is in the predetermined region of one of the menus of the menu system.

7. The method according to claim 1, further comprising the step of determining whether a trigger mechanism is activated while the field of focus of the user is in the predetermined region of the selected one of the menus of the menu system.

8. The method according to claim 1, further comprising the step of positioning at least one of the menus of the menu system in a minimized position when the field of focus of the user is outside the predetermined region of the at least one of the menus.

9. The method according to claim 1, wherein the minimized position is at an edge of a view of the user of the vehicle.

* * * * *